United States Patent [19]

Kirk et al.

[11] Patent Number: 5,390,238
[45] Date of Patent: Feb. 14, 1995

[54] HEALTH SUPPORT SYSTEM

[75] Inventors: Dan M. Kirk; Norman C. Gehring, both of Scottsdale; George J. Butorac, Mesa, all of Ariz.

[73] Assignee: Motorola, Inc., Schaumburg, Ill.

[21] Appl. No.: 898,270

[22] Filed: Jun. 15, 1992

[51] Int. Cl.$^6$ .................... H04M 11/00; G06F 15/00
[52] U.S. Cl. ........................................ 379/93; 379/38; 379/52; 128/904; 364/413.02; 364/413.03; 364/413.04
[58] Field of Search ................ 379/38, 93, 37, 52, 379/106; 364/413.01, 413.02, 413.03, 413.04, 479; 128/1 R, 630, 904, 773, 774; 381/41–46

[56] References Cited

U.S. PATENT DOCUMENTS

| | | | |
|---|---|---|---|
| 4,143,648 | 3/1979 | Cohen et al. | 128/1 R |
| 4,216,462 | 8/1980 | McGrath et al. | 340/150 |
| 4,258,354 | 3/1981 | Carmon et al. | 340/309.4 |
| 4,275,384 | 6/1981 | Hicks et al. | 340/309.4 |
| 4,360,125 | 11/1982 | Martindale et al. | 221/2 |
| 4,370,983 | 2/1983 | Lichtenstein | 128/630 |
| 4,473,884 | 9/1984 | Behl | 364/479 |
| 4,504,153 | 3/1985 | Schollmeyer et al. | 368/10 |
| 4,510,350 | 4/1985 | Wagner et al. | 379/38 |
| 4,572,403 | 2/1986 | Benaroya | 221/3 |
| 4,573,606 | 3/1986 | Lewis et al. | 221/2 |
| 4,674,651 | 6/1987 | Scidmore et al. | 221/3 |
| 4,674,652 | 6/1987 | Aten et al. | 221/3 |
| 4,695,954 | 9/1987 | Rose et al. | 364/413 |
| 4,748,600 | 5/1988 | Urquhart | 368/10 |
| 4,776,016 | 10/1988 | Hansen | 381/42 |
| 4,803,625 | 2/1989 | Fu et al. | 364/413.03 |
| 4,831,562 | 5/1989 | McIntosh et al. | 364/569 |
| 4,838,275 | 6/1989 | Lee | 128/904 |
| 4,928,705 | 5/1990 | Sekhar et al. | 128/773 |
| 4,933,873 | 6/1990 | Kaufman et al. | 364/513.5 |
| 5,036,462 | 6/1991 | Kaufman et al. | 364/413.01 |
| 5,084,828 | 1/1992 | Kaufman et al. | 364/479 |
| 5,197,490 | 3/1993 | Steiner et al. | 128/773 |

OTHER PUBLICATIONS

An article entitled "A Micro-Computer Based System for the Management of the Critically Ill" by H. Comerchero et al. of Mennen Greatbatch Inc., Clarence, N.Y., and by Dr. John W. Hoyt of Naval Regional Medical Center, Portsmouth, Va., IEEE, 1978, pp. 634–644.

An article entitled "A Data Management Program to Assist with Home Monitoring of Blood Glucose and Self Adjustment of Insulin Dosage for Patients with Diabetes Mellitus and Their Physicians"0 by D. Rodbard et al., of the Laboratory of Theoretical and Physical Biology, National Institute of Child Health and Human Development, National Institutes of Health, Bethesda, Md., from IEEE, 1984, pp. 321–324.

An article entitled "Micro–Computer Controlled Care System for the Severely Physically Impaired" by S. J. Sanders et al. of Georgia Institute of Technology, Office of Vice President for Research, Atlanta, Ga., 30332, IEEE, 1984, pp. 886–891.

An article entitled "Solo: An Interactive Microcomputer-Based Bedside Monitor" H. Comerchero et al. of Mennen Greatbatch Inc., Clarence, N.Y., and E. C. Rackow MD et al. of Ellis Hospital, Schenectady, N.Y., IEEE, 1979, pp. 491–498.

Primary Examiner—Curtis Kuntz
Assistant Examiner—Jason Chan
Attorney, Agent, or Firm—Jeffrey D. Nehr

[57] ABSTRACT

A home health and communications support system and method which includes at least one health support unit for monitoring and supporting a patient, at least one monitoring terminal, and a network server coupled between the at least one health support unit and the at least one monitoring terminal for exchanging information between the at least one health support unit and the at least one monitoring terminal. The health support unit comprises a medication controller, communications module for interacting with the patient, central data processor, and external communications interface. The central data processor stores and manipulates patient data generated by the medication controller and by the communications module for patient interaction. The external communications interface allows access to patient data and accepts external data from an external source.

5 Claims, 4 Drawing Sheets ent. It is estimated that 25%
HEALTH SUPPORT SYSTEM

BACKGROUND OF THE INVENTION

This invention relates in general to the field of health care, and in particular to home health care systems and methods.

Patient health care costs are escalating exponentially while the population under care is living longer. Home health care often relies on nurses who are in short supply. Home nursing care is often limited to part-time care, since nursing costs have escalated along with other health care costs.

Many elderly, infirm, disabled or other individuals requiring health care do not wish to leave their home environment, but concern of family members often results in institutionalizing patients to provide health care. One reason is that medication compliance (i.e., adherence to prescribed medication schedules) of the elderly is only about 45%, with a cost of noncompliance of $4 billion per year, according to R. P. Kusserow, Inspector General of the Department of Health and Human Services in Jan., 1989. It is estimated that 25% of present hospitalization of the elderly is due to under medication problems.

Patients are often forced to go to nursing homes or seek some other sort of supervision at great expense, even when their health care needs are relatively simple and routine. Among other worries, family members and health care professionals are concerned about patient forgetfulness (e.g., not remembering to take medication), confusion (e.g., taking an incorrect dosage of medication), wellness monitoring (e.g., making sure the patient has not become incapacitated), and ability to summon help (e.g., sending an alarm in an emergency).

Some home health care units have been proposed to provide apparatus for testing patient temperature or blood pressure, perhaps in combination with a medication scheduling and dispensing apparatus. There are, however, a host of other needs which it would be desirable to meet using a home health support unit. What is desirable is a practical, economical method and apparatus for home health care, which provides in addition to a 24 hour per day medication reminder and controller, speech recognition capability, verification of medication and delivery, remote data accumulation and reporting capability, wellness checking, and an emergency alarm system.

SUMMARY OF THE INVENTION

Accordingly, it is an advantage of the present invention to provide a new and improved apparatus for health care support. It is a further advantage of the present invention to provide a new and improved health care support method. It is still a further advantage of the present invention to provide a method and apparatus for health care support which economically provides medication control, wellness checking and patient data accumulation and reporting capability.

To achieve these advantages, a health care support system is contemplated which includes at least one health support unit for monitoring and supporting a patient, at least one monitoring terminal, and a network server coupled between the at least one health support unit and the at least one monitoring terminal for exchanging information between the at least one health support unit and the at least one monitoring terminal.

The health support unit comprises a medication controller, communications module for interacting with the patient, central data processor, and external communications interface. The communications module for interacting with the patient is coupled to the medication controller. The central data processor is coupled to the medication controller and to the communications module for patient interaction. The external communications interface is coupled to the central data processor. The central data processor is for storing and manipulating patient data generated by the medication controller and by the communications module for patient interaction. The external communications interface is for allowing access to patient data and for accepting external data from an external source.

To also achieve the above advantages, a method for supporting the health of a patient using an electronic health support unit is contemplated, the method comprising the steps of inputting a medication delivery schedule to the health support unit, synthesizing speech in the health support unit to inquire a wellness status of the patient at predetermined intervals and to remind the patient to take medication as scheduled, recognizing patient speech in the health support unit, recording patient data concerning the patient's compliance with the medication delivery schedule and the patient's wellness check results, and transmitting patient data to a central network server for access by the patient's health care provider.

The above and other features and advantages of the present invention will be better understood from the following detailed description taken in conjunction with the accompanying drawings.

DETAILED DESCRIPTION OF THE PREFERRED EMBODIMENT

Figure 1:
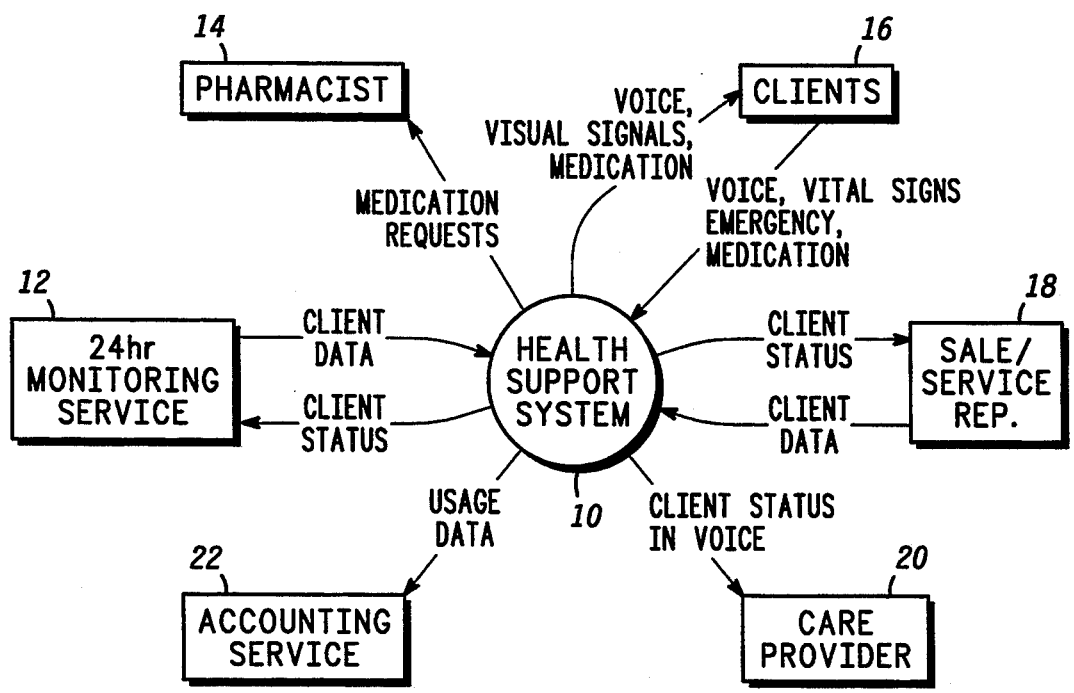
In FIG. 1, there is shown a block system diagram showing direct interfaces for a health support system in accordance with a preferred embodiment of the invention.

The block diagram in FIG. 1 illustrates direct interfaces for a health support system in accordance with a preferred embodiment of the invention. Health support system 10 interacts with 24 hour per day monitoring service 12, pharmacist 14, clients 16, sales and service representatives 18, care providers 20, and accounting service 22.

Sale and service representatives 18 provide input to the health support system 10 by providing initial client 16, or patient data. During the operation of the health support system 10 with respect to a particular client 16, sale and service representatives 18 can check on the client 16 status by accessing the health support system 10.

The health support system 10 provides client 16 support in part by dispensing medication in accordance with a predetermined schedule. The medication requests and scheduling are performed using input from pharmacist 14. In addition, the health support system 10 checks the wellness of the client 16 by monitoring the voice of the client 16 in both prompted and unprompted exchanges. Client 16 voice information indicative of client status (including voice degradation over time) is provided to care provider 20.

Health support system 10 provides data to monitoring service 12. Client 16 data can be sent from monitoring service 12 to the health support system 10, and client 16 status information can be sent from the health support system 10 to the monitoring service 12. Accounting service 22 tracks usage data of clients 16 associated with the health support system 10.

Figure 2:
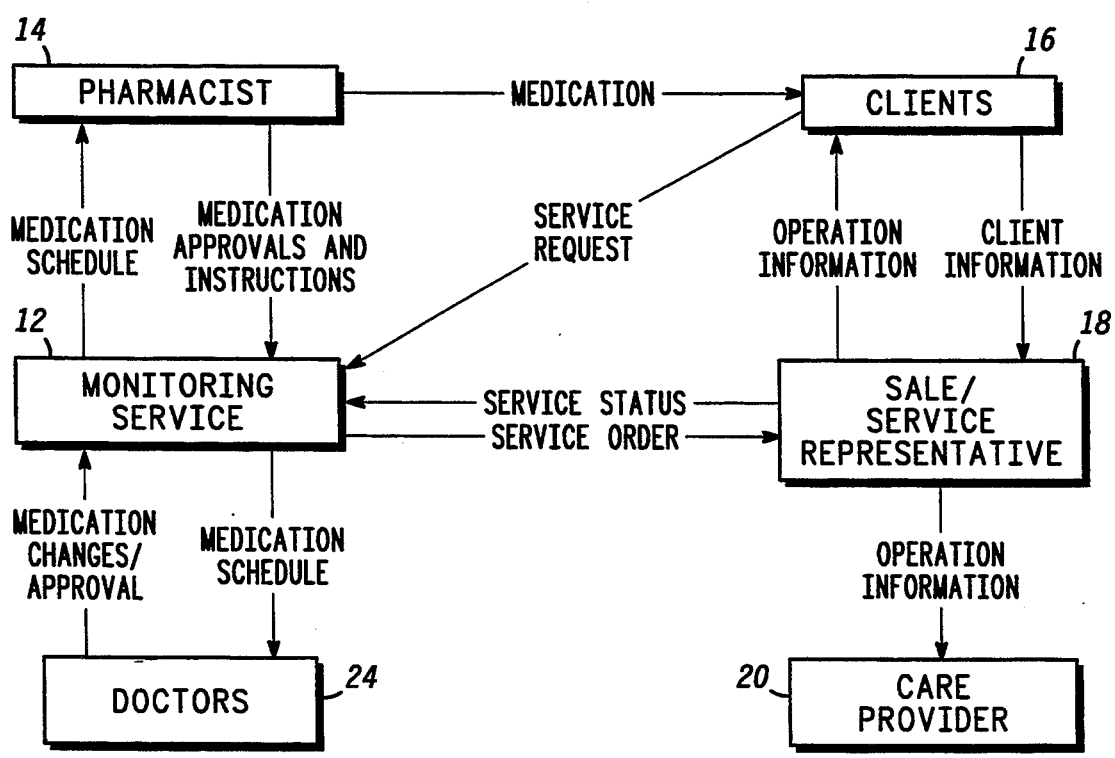
In FIG. 2, there is shown a block system diagram showing indirect interfaces for the health support system as illustrated in FIG. 1.

FIG. 2 illustrates a block diagram of the indirect interfaces for the health support system illustrated in FIG. 1. Doctors 24 provide medication information including medication changes to monitoring service 12 and pharmacist 14. Pharmacist 14 provides medication information to clients 16. Medication approval and instruction information is sent from pharmacist 14 to monitoring service 12 in the form of a service request. Monitoring service 12 checks the medication change order from doctors 24 against the service request from client 16. Client 16 information is sent from clients 16 to sales and service representatives 18. A service status is generated from sales and services representatives 18 to monitoring service 12. In response, monitoring service 12 provides a service order to sales and service representatives 18. Monitoring service 12 also receives medication approval instructions and prescription number information from pharmacist 14, and medication approval information from doctors 24. Monitoring service 12 also generates a medication schedule to doctors 24 and pharmacist 14. The sales and service representative 18 provides operation information to care provider 20 and to the client 16.

Figure 3:
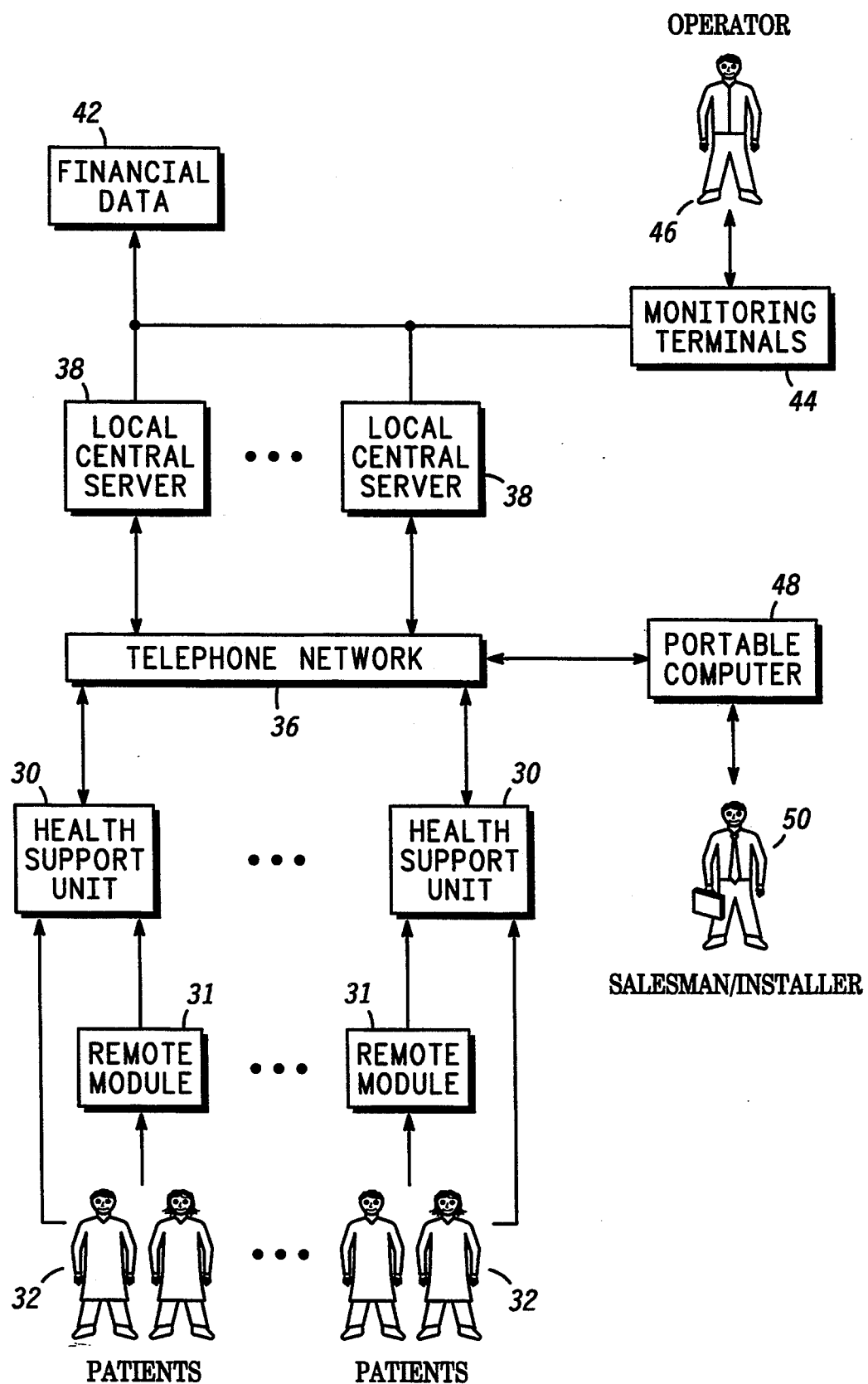
In FIG. 3, there is shown a block diagram of the telephone network, local server, and monitoring terminal interfaces for the health support system illustrated in FIG. 1.

The block diagram in FIG. 3 illustrates the telephone network 36, local server 38, and monitoring terminal 44 interfaces for the health support system 10 illustrated in FIG. 1. The telephone network 36 can be public or private, but is public in the preferred embodiment to minimize costs. Patients 32 provide information via remote modules 31 to health support units 30. Patients may, in addition, provide input directly to health support units 30. Health support units 30 are interfaced through telephone network 36 to local central servers 38, which are computers with memory. Operator 46, through monitoring terminal 44 and a communications link (preferably digital), can access data from local central servers 38, including financial data 42. Salesman/installer 50, through portable computer 48, can also access telephone network 36. Although only two health support units 30 and two local central servers 38 are shown in FIG. 3, many more can be accommodated in this health support system.

Figure 4:
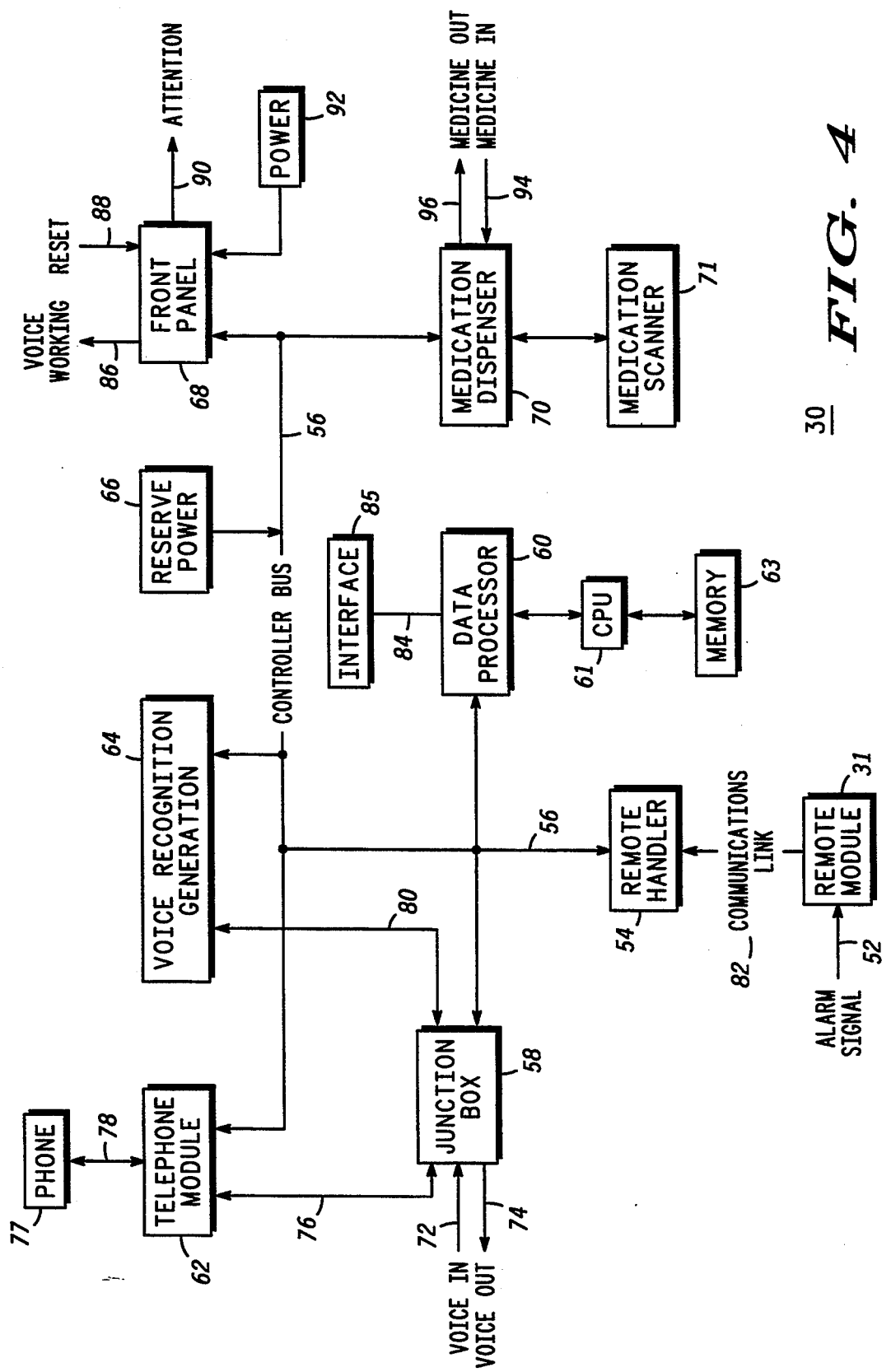
In FIG. 4, there is shown a block diagram of modules comprising a health support unit as part of the health support system shown in FIG. 1.

FIG. 4 illustrates a block diagram of modules comprising a health support unit 30 as part of the health support system 10 shown in FIG. 1. In the preferred embodiment, each health support unit 30 can support up to two patients simultaneously. Controller bus 56 interconnects telephone module 62, voice recognition/generation unit 64, reserve power 66, front panel 68, medication dispenser 70, data processor 60, junction box 58, remote handler 54, and interconnection 84 to interface 85. Interface 85 can be an RS422 interface, providing an interface for system expansion as well as an additional access point to system and patient data. Data processor 60 is coupled to central processing unit (CPU) 61 and memory 63.

In FIG. 4, data processor 60 provides scheduling, control, and verification of medication dispensed and other client 16 information handling. Phone 77 via telephone line 78 provides access to telephone module 62. Voice inputs 72 occur to telephone module 62 via telephone line path 76, or directly to junction box 58. Voice output 74 occurs from the health support unit junction box 58. Voice recognition generation 64 is coupled via path 80 to junction box 58. Power 92 is provided to front panel 68 and the rest of the modules. Front panel 68 comprises voice working function 86, reset function 88, and attention function 90. Loading of medication dispenser 70 is illustrated by medicine insertion arrow 94. Dispensing of medication is shown by medicine withdrawal arrow 96. Medication scanner 71 is coupled to medication dispenser 70 and interfaces with data processor 60 to provide the capability of recognizing what medication is inserted into medication dispenser 70.

As shown in FIG. 4, the patient 32 may initiate alarm signal 52 signalling remote module 31 to provide a communications link 82 to remote handler 54. Remote handler 54 provides a translation of the radio frequency input signal from the communications line 82 to a digital output signal which the remote handler 54 provides to the controller bus 56.

Figure 5:
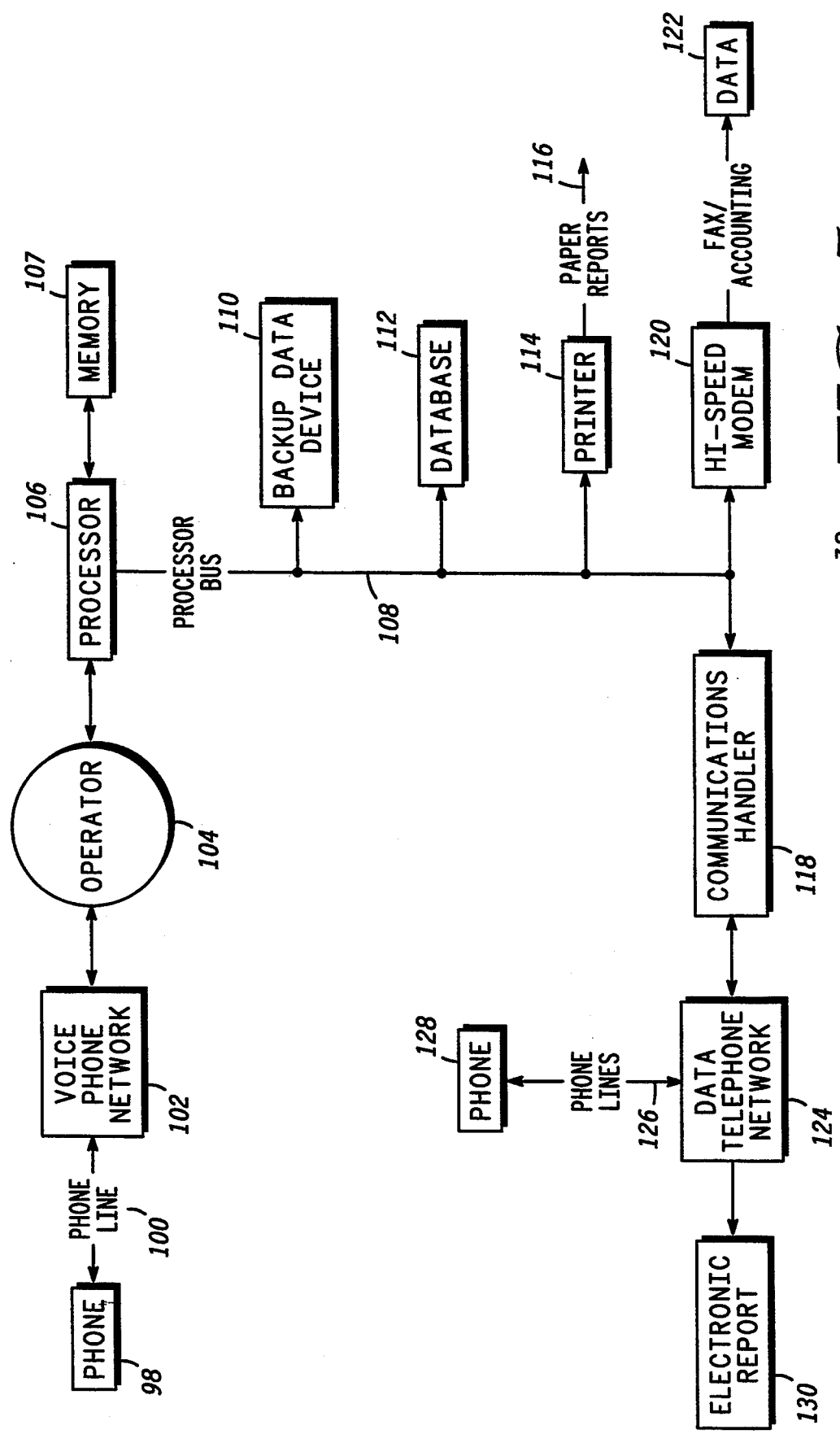
In FIG. 5, there is shown a block diagram of a central server as part of the health support system shown in FIG. 1.

FIG. 5 illustrates a block diagram of the local central server 38 portion of the health support system 10. Phone 98 is coupled through phone line 100 to the voice phone network 102. Operator 104 is an intermediary between voice phone network 102 and processor 106. Processor bus 108 is coupled to processor 106, backup data device 110, data base 112, printer 114, high-speed modem 120, and communications handler 118. Communications handler 118 is coupled to data telephone network 124, which is in turn coupled through phone lines 126 to phones 128 and electronic reporting capability 130. High-speed modem 120 produces data output 122. Printer 114 produces paper reports 116.

Referring to FIG. 4, a representative operational scenario for the health support unit 30, based on a typical day in a patient's 32 life, can be as follows. The health support unit 30 can provide a wake-up call to the patient 32, including sounding a buzzer, flashing a light from front panel 68, based on a wake-up time set by patient 32 preference. The health support unit 30 data processing function 60, performing as a scheduling, compliance and verification monitor, can check the medication to be dispensed 96 to the patient 32 prior to the patient's breakfast and can provide a speech synthesized call 74 to the patient 32 to take that medication 96. The health support unit 30 can instruct the patient 32 on the precise number of pills to be taken from the medication dispenser 70 presented to the patient 32.

The health support unit 30 voice output 74 can suggest a breakfast menu for the patient 32 to eat prior to taking the medication 96 with any medical precautions. For example, it may be important that no orange or other citrus juices be taken prior to ingesting the medication 96. The health support unit 30 voice recognition/generation module 64, through voice out function 74, can act as a speech synthesizer, or recorded speech player, can generally instruct the patient 32 as well on the number of pills to take along with any precautions. The health support unit 30 may further suggest an exercise or exercises to be preformed during the day for the day and any other important daily information.

The health support unit 30 interacts with the patient 32 in a number of ways. For example, the health support unit 30 may receive a command from the patient 32 to dial a family member. The health support unit 30 can connect a speaker and microphone as a speaker telephone through telephone module 62. The health support unit 30 can automatically dial a preprogrammed telephone number and deliver a preprogrammed message to any designated party in the event the patient 32 fails to respond to a wellness inquiry from the voice output 74. The health support unit 30 may also instruct the patient 32 to test the alarm 52 system within the unit 30 by touching a front panel 68 alarm button briefly. The unit 30 can also instruct the patient 32 of other daily event such as nap time, if so desired.

The health support unit 30 also interacts with the local central server 38. The health support unit 30 via telephone module 62, and hence via telephone network 36 and facsimile, telephone, or direct terminal access, reports patient 32 compliance data, self-test status, and receives medication and program schedule updates.

The health support unit 30 can inform the patient 32 as to medications 96 to be taken prior to the lunch and evening meals, as well as suggested menus for those meals. In addition, the patient 32 can be instructed concerning his pre-bedtime medication.

As indicated in the operations scenario above, the health support unit 30 will be located typically in a home environment in a central location so as to insure contact with the patient 32. The health support unit 30 is designed so as not to interfere with other electronic devices located inside the home, and can tolerate dust and moisture in a typical home environment.

Because the health support unit 30 is in the home, a great deal of medication feedback data and home living data may be obtained. The data obtained during interaction with the patient 32 can be forwarded to the central server 38 either in analyzed form or in raw form. The central server 38 can report the results of the analysis of patient 32 status to a doctor 24, care provider 20, or local monitoring service 12. Data of medical interest includes patient 32 data trends, daily activity levels, voice degradation, and medication compliance. By reporting to the doctor 24 on an advisory basis (or as required by the doctor's instructions), a closed loop system of patient care is realized. The data can be transmitted to the doctor 24 via facsimile, paper request, file transfer, or orally via the central station monitor.

The central server 38 can also inform the care provider of the patient's 32 condition and compliance levels. Reports to the care provider 20 in FIG. 2 help determine when the patient 32 has degraded beyond the help of the health support unit 30. Also, the monitoring terminal 44 in FIG. 3 can receive reports from multiple health support units 30 as to their self-test status and medication levels so appropriate action can be taken. Given the close supervision of medication dispensing 96 by the health support unit 30, automatic prescription reordering of long-term medications can be placed by the monitoring terminal 44, e.g., through modem 120 in FIG. 5. Complete control of medication dispenser 70 in FIG. 4 becomes part of the records kept for each patient 32. As shown in FIG. 3, patient data and deviations from prescribed schedules or instructions are stored on local central servers 38, with all deviations reportable through telephone network 36 or through monitoring terminals 44.

Thus, a home health and communications support system and method has been described which overcomes specific problems and accomplishes certain advantages relative to prior art methods and mechanisms. The improvements over known technology are significant. In addition to a 24 hour per day medication reminder and controller, the health support device and method provides speech recognition capability, speech synthesis, verification of medication and delivery, data accumulation and remote reporting capability, wellness checking, and an emergency alarm system.

Thus, there has also been provided, in accordance with an embodiment of the invention, a health support system and method that fully satisfies the aims and advantages set forth above. While the invention has been described in conjunction with a specific embodiment, many alternatives, modifications, and variations will be apparent to those of ordinary skill in the art in light of the foregoing description. Accordingly, the invention is intended to embrace all such alternatives, modifications, and variations as fall within the spirit and broad scope of the appended claims.

What is claimed is:

1. A health support system which comprises:
at least one health support unit for monitoring and supporting a patient, wherein the health support unit comprises:
means for medication control, including:
means for medication verification by comparison with a predetermined medication list;
means for medication scheduling to input a predetermined medication schedule;
means for medication delivery coupled to the means for medication scheduling to dispense medication verified by the means for medication verification according to the predetermined medication schedule; and
means for medication delivery verification to check patient compliance to the predetermined medication schedule;
patient interaction means for communicating with the patient, the patient interaction means coupled to the means for medication control;
central data processing means for storing and manipulating patient data generated by the means for medication control and by the patient interaction means, the central data processing means is coupled to the means for medication control and the patient interaction means;
a communications interface for allowing access to the patient data and for accepting external data from an external source, the communications interface coupled to the central data processing means;
at least one monitoring terminal; and
a network server coupled between the at least one health support unit and the at least one monitoring terminal, the network server for exchanging information between the at least one health support unit and the at least one monitoring terminal, the network server comprising:
a local central server for receiving and transmitting information exchanged between the at least one health support unit and the at least one monitoring terminal;

a telephone network coupled to the local central server, the telephone network for transmitting information between the patient and the local central server; and a communications link for transmitting information between the local central server and the at least one monitoring terminal.

2. A health support system as claimed in claim 1, wherein the patient interaction means comprises:

means for patient voice recognition coupled to the central data processing means, the means for patient voice recognition capable of enabling functions of the health support unit;

means for speech synthesis coupled to the central data processing means, the means for speech synthesis for responding to the patient; and means for wellness monitoring of the patient coupled to the central data processing means.

3. A health support system as claimed in claim 2, wherein the means for wellness monitoring comprises:

an active alarm triggerable by the patient in an emergency; and a passive alarm triggerable by the central data processing means if the patient fails to respond to a predetermined prompt from the means from speech synthesis.

4. A health support system as claimed in claim 1, wherein the central data processing means comprises:

a central processing unit (CPU) for processing patient data and external data; and a memory for storing patient data and external data, the memory coupled to the CPU.

5. A health support system as claimed in claim 1, wherein the communications interface comprises a telephone interface.

* * * * *